United States Patent
Hong et al.

(10) Patent No.: US 10,829,439 B2
(45) Date of Patent: Nov. 10, 2020

(54) METHOD FOR PRODUCING ADIPAMIDE AS INTERMEDIATE FOR PRODUCTION OF RAW MATERIAL FOR BIO-BASED NYLON

(71) Applicants: Hyundai Motor Company, Seoul (KR); Kia Motors Corporation, Seoul (KR)

(72) Inventors: Chae-Hwan Hong, Seoul (KR); Na-Kyong Yun, Gyeonggi-do (KR); Ha-Eun Jeong, Gyeonggi-do (KR); Sung-Wan Jeon, Gyeonggi-do (KR)

(73) Assignees: Hyundai Motor Company, Seoul (KR); Kia Motors Corporation, Seoul (KR)

( * ) Notice: Subject to any disclaimer, the term of this patent is extended or adjusted under 35 U.S.C. 154(b) by 70 days.

(21) Appl. No.: 16/197,659

(22) Filed: Nov. 21, 2018

(65) Prior Publication Data

US 2020/0071262 A1    Mar. 5, 2020

(30) Foreign Application Priority Data

Aug. 28, 2018    (KR) .................. 10-2018-0101432

(51) Int. Cl.
| | | |
|---|---|---|
| *C07C 231/12* | (2006.01) | |
| *B01J 23/656* | (2006.01) | |
| *B01J 23/42* | (2006.01) | |
| *B01J 23/10* | (2006.01) | |
| *C07C 51/06* | (2006.01) | |
| *B01J 35/00* | (2006.01) | |
| *C08G 69/26* | (2006.01) | |
| *C07C 231/02* | (2006.01) | |
| *B01J 21/08* | (2006.01) | |

(52) U.S. Cl.
CPC ............ *C07C 231/12* (2013.01); *B01J 21/08* (2013.01); *B01J 23/10* (2013.01); *B01J 23/42* (2013.01); *B01J 23/6567* (2013.01); *B01J 35/0066* (2013.01); *C07C 51/06* (2013.01); *C07C 231/02* (2013.01); *C08G 69/26* (2013.01)

(58) Field of Classification Search
CPC ....... C07C 51/06; C07C 55/14; C07C 231/12; C07C 231/02; C08G 69/26
See application file for complete search history.

(56) References Cited

U.S. PATENT DOCUMENTS

| | | | | |
|---|---|---|---|---|
| 2010/0317823 A1* | 12/2010 | Boussie | ................. | B01J 23/464 |
| | | | | 528/323 |
| 2013/0225785 A1* | 8/2013 | Dias | ..................... | C07D 223/10 |
| | | | | 528/323 |
| 2017/0158593 A1* | 6/2017 | Boussie | ................... | B01J 23/40 |

OTHER PUBLICATIONS

Smith et al "Modifications in the nitric acid oxidation of D-glucose", Carbohydrate Research 350 (2012) 6-13, Available online Jan. 4, 2012.*

Chen et al "Synthesis of Stereoregular Head,Tail Hydroxylated Nylons Derived from D-Glucose", J. Org. Chem. 1996, 61, 5847-5851, Apr. 1996.*

* cited by examiner

*Primary Examiner* — Gregory Listvoyb
(74) *Attorney, Agent, or Firm* — Mintz Levin Cohn Ferris Glovsky and Popeo, P.C.; Peter F. Corless (57) ABSTRACT

Disclosed is a method for producing adipamide, which may include the steps of: (a) reacting glucose, nitric acid ($HNO_3$), sodium nitrite ($NaNO_2$) and potassium hydroxide (KOH) to produce a glucaric acid potassium salt, (b) producing glucamide by reacting the glucaric acid potassium salt, with an acidic solution and removing a potassium ion from the glucaric acid potassium salt, (c) preparing an reaction admixture by adding the glucamide and a catalyst to hydrogen halide and acetic acid, and (d) treating the reaction admixture with hydrogen gas in a reactor thereby producing the adipamide.

19 Claims, 6 Drawing Sheets

METHOD FOR PRODUCING ADIPAMIDE AS INTERMEDIATE FOR PRODUCTION OF RAW MATERIAL FOR BIO-BASED NYLON

CROSS-REFERENCE(S) TO RELATED APPLICATIONS

This application claims priority to Korean Patent Application No. 10-2018-0101432, filed on Aug. 28, 2018, which is incorporated herein by reference in its entirety.

TECHNICAL FIELD

The present invention relates to a novel method of producing adipamide, which is used as an intermediate for production of adipic acid which is used in various applications such as a raw material for nylon, by using biomass-derived glucose as a starting material. The method may include: producing a glucaric acid potassium salt using glucose as a starting material; producing glucamide using the glucaric acid potassium salt; and producing adipamide using the glucamide at high temperature in an atmosphere of high-pressure hydrogen in the presence of a specific catalyst.

BACKGROUND OF THE INVENTION

Among various nylon materials, nylon 66, which is a representative nylon material together with nylon 6, is in great demand because of its excellent physical properties, but process technology for producing nylon 66 using biomass as raw material has not yet been established. Thus, the development of a process for producing bio-based nylon 66 can be expected to have a remarkable ripple effect not only in an economic terms but also in environmental terms.

Nylon 66 has excellent heat resistance, abrasion resistance and chemical resistance, and is used in parts requiring high temperature characteristics among automobile parts. In addition, nylon 66 is the next most used after nylon 6 among nylons which are used in mobile parts. Nylon 66 is produced by polycondensation between hexamethylenediamine and adipic acid. Adipic acid, which is used as a monomer in nylon 66 production, is currently produced through a chemical synthesis process using, as an intermediate, cyclohexanone synthesized from benzene which is obtained during crude oil refining. However, this petroleum-based production process causes problems such as instability of oil prices, use of benzene that is a toxic substance, generation of environmental pollution by-products including nitric oxide (NOx), and the like, and thus needs to be replaced with bio-based technology. Therefore, the production of nylon using a bio-based process can simultaneously exhibit the effect of reducing the dependence of raw materials on petroleum and the effect of reducing the generation of environmental pollutants.

SUMMARY OF THE INVENTION

The present invention has been made keeping in mind the above-described problems, and is directed to a first technology of synthesizing adipamide, which can be used for production of adipic acid, by use of glucose.

It is an object of the present invention to provide an important process to improve synthesizing adipic acid using glucose derived from terrestrial plant resources.

In an aspect, the present invention provides a method for producing adipamide. The method may include the steps of: (a) producing a glucaric acid potassium salt by one or more steps comprising reacting glucose, nitric acid ($HNO_3$), sodium nitrite ($NaNO_2$) and potassium hydroxide (KOH); (b) producing glucamide by reacting the glucaric acid potassium salt, produced in step (a), and an acidic solution and removing a potassium ion from the glucaric acid potassium salt; (c) preparing a reaction admixture by adding the glucamide, produced in step (b), and a catalyst to hydrogen halide (e.g., HBr) and acetic acid; and (d) treating the reaction admixture with hydrogen gas in a reactor thereby producing adipamide.

In preferred aspect, in the step (c), the halogen halide and the acetic acid may be combined or mixed in a reaction solution for preparing the reaction admixture.

In preferred aspect, in the step (d), the reaction admixture may be treated by introducing the reaction admixture into the reactor and reacting thereof with the hydrogen gas.

The method, in the step (a), may include the steps of: preparing a reactant by reacting sodium nitrite ($NaNO_2$) and a first mixture including glucose and nitric acid ($HNO_3$); preparing a basic reactant having a pH of about 9 to 10 by adding potassium hydroxide (KOH) to the reactant; preparing an acidic reactant having a pH of about 3 to 4 by adding nitric acid ($HNO_3$) to the basic reactant; and precipitating the acidic reactant, and filtering and washing the formed precipitate to obtain a glucaric acid potassium salt.

In step (a), the sodium nitrite ($NaNO_2$) and the first mixture may be reacted at a temperature of about 0° C. to 30° C.

When the reaction temperature in this step is less than about 0° C., the reaction temperature may not be reached, and thus reactivity may be decreased. On the other hand, when the reaction temperature is greater than about 30° C., unnecessary by-products may be generated, and yield may not be increased.

In step (a), sodium nitrite ($NaNO_2$) and glucose may suitably be mixed at a weight ratio of about 1:500 to 1:1500. Preferably, sodium nitrite ($NaNO_2$) and glucose may be mixed at a weight ratio of about 1:1000.

The sodium nitrite ($NaNO_2$) as used herein may induce crystals of the glucaric acid potassium salt. For this reason, when the mixing ratio between sodium nitrite and glucose may be out of the above-described mixing ratio, crystals of the glucaric acid potassium salt to be obtained in step (a) may not be properly formed.

Therefore, the reactant prepared in the step of preparing the reactant may be basified to basic pH by addition of potassium hydroxide (KOH), and then acidified to acidic pH by addition of nitric acid ($HNO_3$). Next, the acidic reactant may be allowed to stand in ethanol, thereby producing a glucaric acid potassium salt which is an acid-base reaction product.

Step (b) may include the steps of: removing a potassium ion from the glucaric acid potassium salt, produced in step (a), by reacting a second mixture comprising the glucaric acid potassium salt and a reaction solvent with the acidic solution; and adding an aqueous ammonia solution to a substance from which the potassium ion was removed in the step of removing the potassium ion, followed by mixing for a predetermined time, and then adding ethanol thereto to precipitate glucamide particles, and recovering the precipitated glucamide particles. Preferably, the acidic solution for the reaction with the glucaric acid potassium salt may be in a reaction solvent.

The reaction solvent that is used in the step of removing the potassium ion may be any one or more selected from the group consisting of C1 to C10 primary alcohols and secondary alcohols. Among these alcohols, methanol is most preferably used.

The acidic solution may suitably be sulfuric acid ($H_2SO_4$) or para-toluene sulfuric acid.

The reaction in the step of removing the potassium ion may be suitably performed for about 12 to 24 hours. When the reaction is performed for less than about 12 hours, the potassium ion may not be properly removed, and thus the yield of glucamide may be decreased, and when the reaction time is greater than about 24 hours, process cost may be increased without increasing yield so that economic efficiency may be reduced.

The aqueous ammonia solution may suitably have an ammonia concentration of about 25 wt % to 28 wt % based on the total weight of the he aqueous ammonia solution.

Step (c) and step (d) may include steps of preparing adipamide from the glucamide produced in step (b). In step (c), a reaction admixture may be prepared by adding the glucamide produced in step (b) and a catalyst to hydrogen bromide (HBr) and acetic acid. In step (d), the reaction admixture and hydrogen gas may be reacted in a reactor thereby producing the adipamide.

The hydrogen bromide in the step (c) may be included in an amount of 1 vol % to 2 vol % relative to the acetic acid.

The glucamide in step (c) may be added in an amount of 1 wt % to 2 wt % based on the total weight of the halogen halide and the acetic acid.

The catalyst in step (c) may suitably include a RePd/$CeO_2$ catalyst or a Pt/$SiO_2$ catalyst. The RePd/$CeO_2$ catalyst may include an amount of about 2 wt % to 10 wt % of rhenium (Re) and an amount of about 1 wt % to 3 wt % of palladium (Pd) based on the total weight of cerium oxide ($CeO_2$). The Pt/$SiO_2$ catalyst may include an amount of about 1 wt % to 5 wt % of platinum (Pt) based on the total weight of silica ($SiO_2$).

The reaction admixture may suitably include the catalyst in step (c) in an amount of about 0.3 wt % to 0.5 wt % based on the total weight of the reaction admixture.

In step (d), the reaction admixture prepared in step (c) may be introduced into a reactor and allowed to react for a predetermined time. The hydrogen gas in step (d) may be introduced into the reactor such that an internal pressure of the reactor is about 30 bar to 50 bar.

The reaction in step (d) may be performed at a temperature of about 120° C. to 150° C. for about 2 to 10 hours, thereby producing adipamide.

Further provided is a method of producing an adipic acid. The method may include the steps of producing adipamide as described herein.

Also provided is a nylon product including an adipic acid produced by the method as described herein.

Other aspects of the inventions are disclosed infra.

DETAILED DESCRIPTION

Hereinafter, preferred embodiments of the present invention will be described in detail with reference to the accompanying drawings.

Hereinafter, preferred embodiments of the present invention will be described in detail with reference to the accompanying drawings. However, these embodiments are provided for illustrative purposes only and that various changes and modifications may be made by those skilled in the art to which the present invention pertains. Thus, the scope of the present invention is not limited to the embodiments disclosed herein.

The terminology used herein is for the purpose of describing particular embodiments only and is not intended to be limiting. As used herein, the singular forms "a," "an" and "the" are intended to include the plural forms as well, unless the context clearly indicates otherwise. It will be further understood that the terms "comprise", "include", "have", etc. when used in this specification, specify the presence of stated features, regions, integers, steps, operations, elements and/or components but do not preclude the presence or addition of one or more other features, regions, integers, steps, operations, elements, components, and/or combinations thereof.

Further, unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Furthermore, the number of repeats of each step, process conditions, and the like, are not particularly limited as long as they do not impair the object of the present invention.

In addition, unless otherwise defined, all terms used herein, including technical or scientific terms, have the same meanings as commonly understood by those skilled in the art to which this invention pertains.

Figure 1:
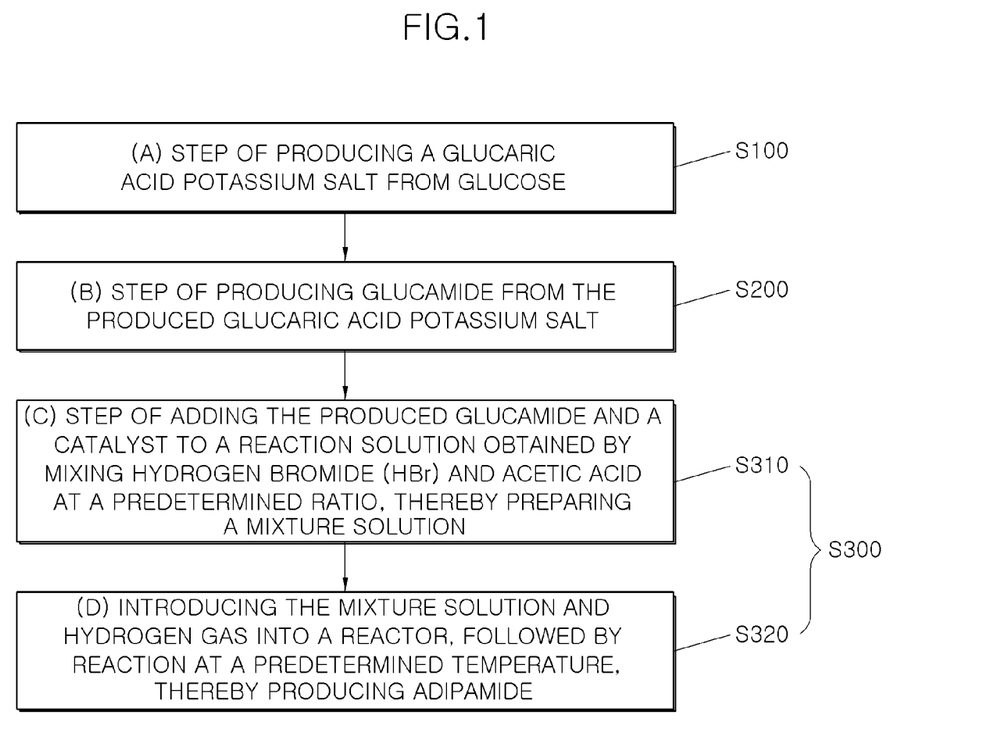
FIG. 1 is a flowchart showing a method for producing adipamide according to the present invention.

As shown in FIG. 1, the method for producing adipamide according to an exemplary embodiment of the present invention may include the steps of: (a) producing a glucaric acid potassium salt from glucose (S100); (b) producing glucamide from the produced glucaric acid potassium salt (S200); (c) and (d) producing adipamide from the produced glucamide (S300).

Figure 5:
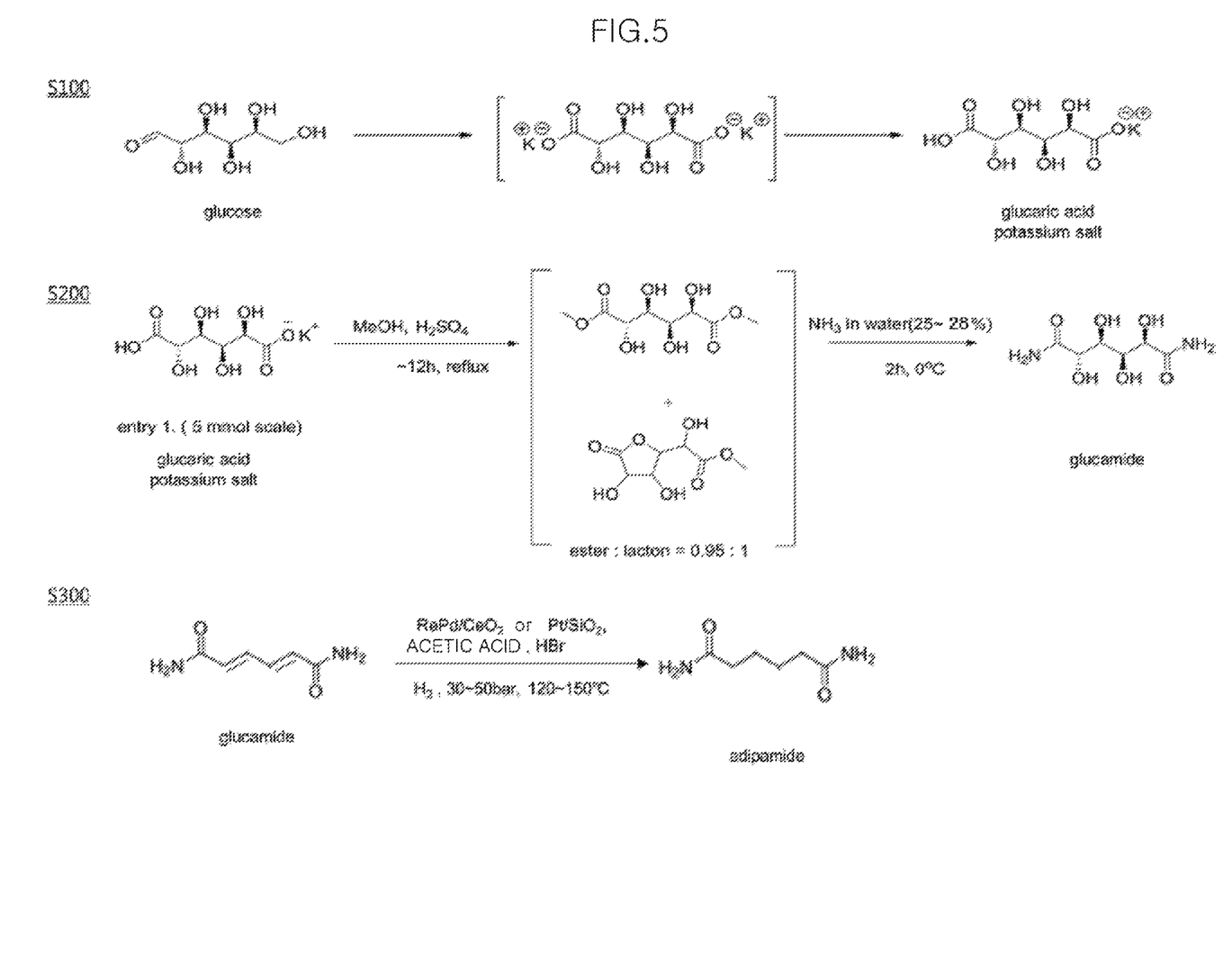
FIG. 5 is a sequential reaction scheme showing a process of producing adipamide from glucose according to an embodiment of the present invention.

In step (S100) of producing a glucaric acid potassium salt from glucose, as shown in reaction scheme 1 below, a glucaric acid potassium salt may be produced from glucose used as a starting material. Glucose t may preferably be glucose derived from terrestrial plant resources that are biomass, but is not limited thereto, and glucose that is generally used in the art may also be used in this step.

Reaction Scheme 1 glucose glucaric acid potassium salt

Figure 2:
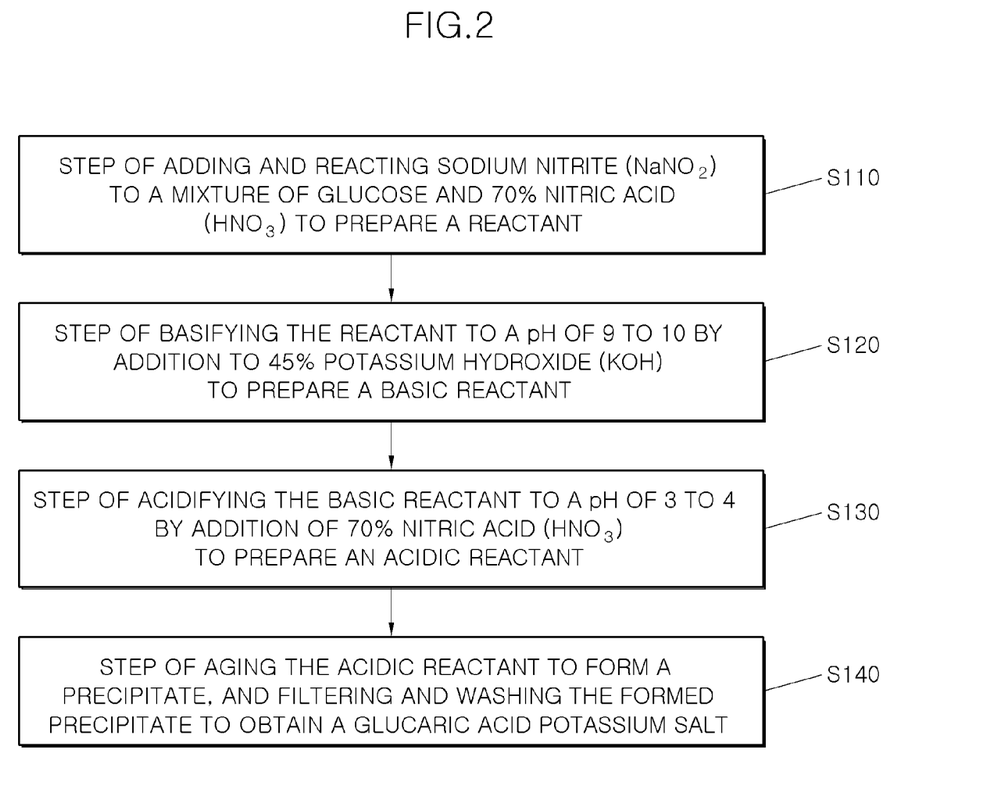
FIG. 2 is a detailed flowchart showing step (S100) of producing a glucaric acid potassium salt from glucose in the method for producing adipamide according to the present invention.

In an exemplary embodiments, as shown in FIG. 2, step S100 may include the steps of: (S110) preparing a reactant by reacting sodium nitrite ($NaNO_2$) to a first mixture of glucose and nitric acid ($HNO_3$); (S120) preparing a basic reactant having a pH of about 9 to 10 by adding of potassium hydroxide (KOH) to the reactant; (S130) preparing an acidic reactant having a pH of about 3 to 4 by adding nitric acid ($HNO_3$) to the basic reactant; and (S140) precipitating the acidic reactant, and filtering and washing the formed precipitate, thereby obtaining a glucaric acid potassium salt.

For example, step (S110) may include adding 10 to 15 g of glucose to 13 ml of 70% nitric acid ($HNO_3$) to prepare a mixture, and 10 to 20 mg of sodium nitrite ($NaNO_2$) to the mixture, thereby preparing a reactant.

The reaction in the step of preparing the reactant may preferably be performed at a temperature of about 0° C. to 30° C. When the reaction temperature is less than about 0° C., the reaction temperature may not be reached, and thus reactivity may be decreased. On the other hand, when the reaction temperature is greater than about 30° C., unnecessary by-products may be generated, and thus an effect such as an increase in yield may not be obtained.

In step (S110), sodium nitrite and glucose may be mixed at a weight ratio of about 1:500 to 1:1500, or particularly of about 1:1000.

In step (S120), the reactant prepared in step (S110) may be basified to a pH of about 9 to 10 by adding about 45% potassium hydroxide, thereby preparing a basic reactant.

When the basic pH in step (S120) is out of the above-described basic pH range, for example, less than about 9, or greater than about 10, the glucaric acid potassium salt may not be properly formed.

The basic reactant prepared in step (S120) may be acidified to a pH of about 3 to 4 by adding about 70% nitric acid ($HNO_3$), thereby preparing an acidic reactant (S130).

Thereafter, the prepared acidic reactant may be aged at room temperature (e.g., 15 to 30° C.) for 12 hours to precipitate formed solid particles, and the precipitate may be washed with methanol, thereby obtaining a highly pure glucaric acid potassium salt (S140).

In step (S120) of preparing the basic reactant and step (S130) of preparing the acidic reactant, the pH of the reactant may be measured by pH paper, but is not necessarily limited thereto, and the pH may also be measured by a pH measurement method that is generally used in the art.

Figure 3:
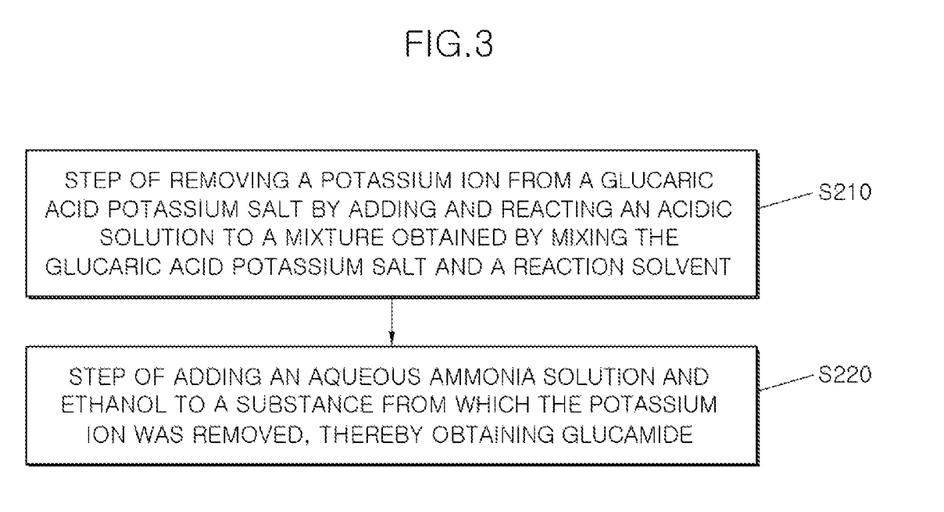
FIG. 3 is a detailed flowchart showing step (S200) of producing glucamide from a glucaric acid potassium salt in the method for producing adipamide according to the present invention.

As shown in FIG. 3, step (S200) of producing glucamide from the glucaric acid potassium salt produced in step (S100) may include the steps of: (S210) removing a potassium ion from the glucaric acid potassium salt by reacting a second mixture including the glucaric acid potassium salt with an acidic solution, which may be preferably in a reaction solvent, followed by reaction; (S220) adding an aqueous ammonia solution and ethanol to the glucaric acid from which the potassium ion was removed, thereby obtaining glucamide particles.

For example, in step (S210), an amount of 1.24 g (5 mmol) of the glucaric acid potassium salt may be added to and mixed with methanol used as a reaction solvent. The reaction solvent that is used in this step may be any one or more primary alcohols and secondary alcohols. However, alcohols other than methanol have a problem in that the yield of the substance to be obtained in a subsequent process is reduced rapidly. For this reason, methanol may be suitably used.

Subsequently, about 0.3 to 1.0 ml of sulfuric acid ($H_2SO_4$) as an acidic solution may be added slowly to the mixture. As the acidic solution, para-toluene sulfuric acid may suitably be used instead of sulfuric acid.

The acidic solution that is added in step (S210) may detach a potassium (K) ion from the glucaric acid potassium salt. Thus, the reaction may be maintained for about 12 to 24 hours so that the potassium ion may be properly removed. Then, the reaction may be cooled at room temperature (15 to 30° C.) to form a potassium sulfate ($K_2SO_4$) salt precipitate which is then removed by filtration.

In step (S220) of recovering glucamide particles, methanol used as the reaction solvent may be removed by evaporation from the glucaric acid from which the potassium (K) ion was removed in step (S210). Then, while the reactor containing the glucaric acid from which methanol was evaporated out is maintained in a bath at a temperature of 0° C., about 10 ml of an aqueous ammonia solution may be added to the glucaric acid and stirred for about 2 to 4 hours. 150 ml of ethanol may be added to the mixture which may be then stirred for 10 and allowed to stand for 10 minutes, thereby obtaining glucamide particles.

The aqueous ammonia solution may suitably be a solution obtained by dissolving ammonia ($NH_3$) in water at a concentration of about 25 to 28 wt %.

For example, in step (S200), as shown in reaction scheme 2 below, glucamide may be produced from the glucaric acid potassium salt by: removing a potassium (K) ion from the glucaric acid potassium salt by adding 0.3 ml of sulfuric acid ($H_2SO_4$) slowly to a solution of 1.24 g (5 mmol) of the glucaric acid potassium salt in 150 ml of methanol, followed by reaction for 12 hours; completely removing methanol by evaporation from the glucaric acid from which the potassium (K) ion was removed; adding 10 ml of an aqueous ammonia ($NH_3$) solution to the glucaric acid from which methanol was evaporated out, followed by stirring for 2 hours while maintaining the reactor containing the glucaric acid in a bath at a low temperature of 0° C.; and then adding 150 ml of ethanol to the mixture, followed by stirring for 10 minutes and allowing to stand for 10 minutes.

Reaction Scheme 2 entry 1. (.5 mmol scale)

glucaric acid potassium salt ester: lacton = 0.95:1 glucamide

Figure 4:
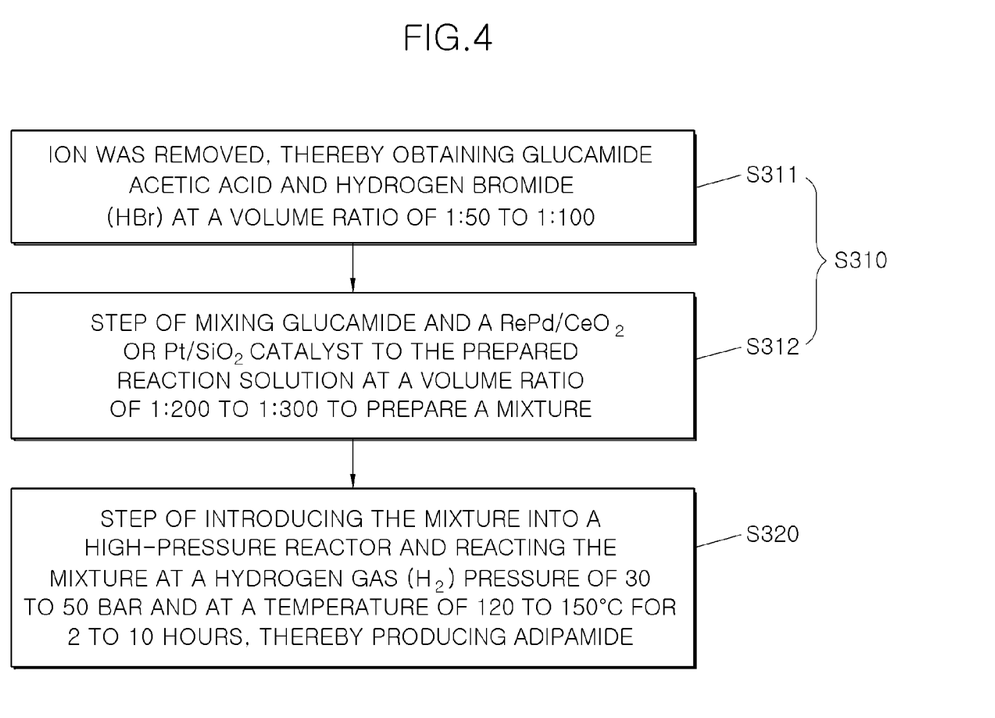
FIG. 4 is a detailed flowchart showing step (S300) of producing adipamide from glucamide in the method for producing adipamide according to the present invention.

As shown in reaction scheme 3 below, in step (S300), adipamide may be produced from the glucamide produced in step (S200). For example, as shown in FIG. 4, step (S300) may include the steps of: (S311) mixing acetic acid and hydrogen bromide (HBr) at a predetermined ratio to prepare a reaction solution; (S312) adding the glucamide and a catalyst to the prepared reaction solution to prepare a reaction admixture; and (S320) introducing the reaction admixture into a reactor and allowing the mixture to react at high temperature in an atmosphere of high-pressure ($H_2$) gas, thereby producing adipamide.

Reaction Scheme 3 glucamide adipamide

Step (S311) is a step of preparing a reaction solution required for producing adipamide from the glucamide. In this step, acetic acid may be used as a solvent, and the reaction solution may include hydrogen bromide (HBr) in an amount of about 1 to 2 vol % relative to acetic acid and may be prepared by mixing.

The present invention is characterized in that an acidic solvent is used as the solvent of the reaction solution. Generally, acidic solvents include hydrochloric acid, sulfuric acid and the like. In the step of producing adipamide according to the present invention, the glucamide may be reactive only in acetic acid, and a reaction for producing adipamide may not occur. For this reason, the present invention is characterized by using acetic acid.

In step (S312), the glucamide produced in step S200 and a catalyst may be added to the reaction solution prepared in step (S311), thereby preparing the reaction admixture. In this step, the glucamide may be added in an amount of about 1 to 2 wt % based on the total weight of the reaction solution.

When the amount of glucamide added is out of the above-described range, for example, less than about 1 wt % or greater than about 2 wt %, reactivity for producing adipamide may decrease rapidly.

Furthermore, the catalyst that is used in the reaction admixture may be a RePd/$CeO_2$ catalyst. For example, Re and Rd may be carried on cerium oxide ($CeO_2$) based on the total weight of the cerium oxide. Preferably, an amount of about 2 to 12 wt % of rhenium (Re) and an amount of about 1 to 3 wt % of palladium (Pd) may be loaded on the $CeO_2$. Alternatively, the catalyst may be a Pt/$SiO_2$ catalyst. For example, Pt may be carried on silica ($SiO_2$) based on the total weight of the silica. Preferably, an amount of about 1 to 5 wt % of platinum (Pt) may be loaded on the $SiO_2$.

The RePd/$CeO_2$ catalyst or the Pt/$SiO_2$ catalyst may be contained in an amount of about 0.3 to 0.5 wt % based on the total weight of the reaction admixture.

The catalyst tin step (S310) of the present invention as described above may be prepared as described below.

An example of a method for preparing the RePd/$CeO_2$ catalyst is as follows. Ammonium perrhenate (LS-Nikko Copper Inc., Korea), a precursor of rhenium (Re), is dissolved in water, and then the aqueous solution of the rhenium (Re) precursor ammonium perrhenate is added to spherical $CeO_2$ particles (Sigma Aldrich, USA) as a carrier such that the ammonium perrhenate is loaded on the carrier in an amount of 10 wt % based on the total weight of the carrier. The loaded material is dried at a temperature of about 100° C. Next, a solution of the palladium (Pd) precursor $PdCl_2$ (Sigma Aldrich, USA) is added to the $CeO_2$ particles such that the palladium precursor is loaded on the carrier in an amount of 3 wt % based on the total weight of the carrier, followed by drying at a temperature of about 100° C. Next, the $CeO_2$ particles loaded with rhenium (Re) and palladium (Pd) by loading the predetermined amounts of the rhenium (Re) precursor and the palladium (Pd) precursor are calcined at a temperature of about 300° C., and then subjected to a reduction reaction in a hydrogen gas atmosphere at a temperature of 300° C., thereby preparing a RePd/CeO$_2$ catalyst.

A method for preparing the Pt/SiO$_2$ catalyst which is another catalyst is as follows. A solution of the platinum (Pt) precursor tetraammineplatinum nitrate (Sigma Aldrich, USA) in water is added to spherical SiO$_2$ particles (Sigma Aldrich, USA) as a carrier such that the tetraammineplatinum nitrate is loaded on the carrier in an amount of 5 wt % based on the total weight of the carrier. The loaded material is dried at a temperature of about 100° C., and then calcined at a temperature of about 300° C. and subjected to a reduction reaction in a hydrogen gas atmosphere at a temperature of about 300° C., thereby preparing a Pt/SiO$_2$ catalyst.

In step (S320), adipamide may be produced by introducing the prepared reaction admixture into a reactor and the reaction admixture may be subjected to a hydrogenation reaction. For example, the reaction admixture may be introduced into a reactor, and then allowed to react at a temperature of about 120 to 150° C. for about 2 to 10 hours while hydrogen gas is introduced into the reactor at a pressure of about 30 to 50 bar.

When the hydrogen gas pressure in step (S320) is out of the above-described range, for example, less than about 30 or greater than about 50 bar, the hydrogenation reaction may not properly occur, and thus the yield of adipamide may decrease.

Furthermore, when the reaction time in step (S320) is less than about 2 hours, the yield of adipamide may be reduced due to a short reaction time, and when the reaction time is greater than about 10 hours, the overall production process time may be increased due to an excessively long reaction time and productivity may be reduced.

In addition, the reaction temperature in step (S320) may be less than about 120° C., hydrogenation reactivity may decrease, and when the reaction temperature is greater than about 150° C., production of by-products may increase to reduce production efficiency. For these reasons, the hydrogenation reaction may preferably be performed at a temperature ranging from 120° C. to 150° C. as described above.

Hereinafter, the present invention will be described in further detail with reference to examples, comparative examples and test examples. It is to be understood, however, that these examples are for illustrative purposes only and the present invention is not limited to these examples and may be modified and changed in various ways.

Tables 1 and 2 below summarize the kind of solvent used in each of examples and comparative examples, reaction conditions, and the production of adipamide in step (S300) of producing adipamide according to the present invention.

In the following Tables 1 and 2, (A) indicates the kind of acidic solution as a reaction solution and whether hydrogen bromide (HBr) is added, and (B) indicates the hydrogen bromide (HBr)/acidic solvent (acetic acid) ratio (v/v) in the reaction solution.

TABLE 1

|  | (A) | (B) | Catalyst | Reaction temperature (° C.) | H$_2$ pressure (bar) | Reaction time (hours) | Synthesis of adipamide |
|---|---|---|---|---|---|---|---|
| Example 1 | Acetic acid, HBr | 1/100 | RePd/CeO$_2$ | 135 | 30 | 3 | ○ |
| Example 2 | Acetic acid, HBr | 1/100 | RePd/CeO$_2$ | 140 | 30 | 4 | ○ |
| Example 3 | Acetic acid, HBr | 1/50 | Pt/SiO$_2$ | 145 | 30 | 5 | ○ |
| Example 4 | Acetic acid, HBr | 1/50 | Pt/SiO$_2$ | 150 | 30 | 6 | ○ |

TABLE 2

|  | (A) | (B) | Catalyst | Reaction temperature (° C.) | H$_2$ pressure (bar) | Reaction time (hours) | Synthesis of adipamide |
|---|---|---|---|---|---|---|---|
| Comparative Example 1 | Acetic acid, HBr | 1/100 | SiO$_2$ | 135 | 30 | 1 | X |
| Comparative Example 2 | Acetic acid, HBr | 1/50 | Al$_2$O$_3$ | 135 | 30 | 2 | X |
| Comparative Example 3 | Acetic acid, HBr | 1/50 | CeO$_2$ | 130 | 30 | 3 | X |
| Comparative Example 4 | Acetic acid | — | RePd/CeO$_2$ | 125 | 30 | 4 | X |
| Comparative Example 5 | Acetic acid | — | Pt/SiO$_2$ | 125 | 30 | 5 | X |
| Comparative Example 6 | Acetic acid, HBr | 1/50 | RePd/CeO$_2$ | 50 | 30 | 6 | X |
| Comparative Example 7 | Acetic acid, HBr | 1/30 | RePd/CeO$_2$ | 135 | 30 | 3 | X |
| Comparative Example 8 | Acetic acid, HBr | 1/30 | Pt/SiO$_2$ | 125 | 30 | 5 | X |
| Comparative Example 9 | Acetic acid, HBr | 1/200 | RePd/CeO$_2$ | 135 | 30 | 3 | X |
| Comparative Example 10 | Acetic acid, HBr | 1/200 | Pt/SiO$_2$ | 125 | 30 | 5 | X |
| Comparative Example 11 | Hydrochloric acid, HBr | 1/100 | RePd/CeO$_2$ | 135 | 30 | 3 | X |
| Comparative Example 12 | Sulfuric acid, HBr | 1/100 | RePd/CeO$_2$ | 135 | 30 | 3 | X |

Comparative Examples 1 to 12 in Table 2 above are examples that do not satisfy each reaction condition used in step (S300) of producing adipamide from glucamide in the adipamide production method of the present invention. The results of these Comparative Examples will now be described in detail.

In Comparative Examples 1 to 3, $CeO_2$ or $SiO_2$ alone, which is the carrier of the catalyst used in the present invention, was used, or aluminum oxide ($Al_2O_3$) which is a conventional catalyst was used. In these Comparative Examples, hydrogenation reactivity was low, and thus the synthesis of adipamide was not properly achieved.

In Comparative Examples 4 and 5, hydrogen bromide (HBr) was not added to the reaction solution. In this Comparative Example, adipamide was not synthesized, suggesting that the addition of hydrogen bromide (HBr) is essential for carrying out the hydrogenation reaction in the present invention.

In Comparative Example 6, the reaction in the reactor was performed at a temperature of 50° C. which is less than the lower limit of the temperature range proposed in the present invention. In this Comparative Example, a sufficient amount of heat required for the reaction was not supplied due to the low reaction temperature so that reactivity was low, and for this reason, adipamide was not synthesized.

In Comparative Examples 7 to 10, the mixing ratio of hydrogen bromide (HBr) to acetic acid in the reaction solution was out of the range proposed in the present invention. In these Comparative Examples, hydrogenation reactivity was low, and for this reason, adipamide was not synthesized.

In Comparative Examples 11 and 12, hydrochloric acid or sulfuric acid was used instead of acetic acid as the acidic solvent in the reaction solution. As can be seen from the results in the Table 2 above, when acidic solvent other than acetic acid was used in the reaction solution, the reaction did not proceed, and thus adipamide was not synthesized.

Figure 6:
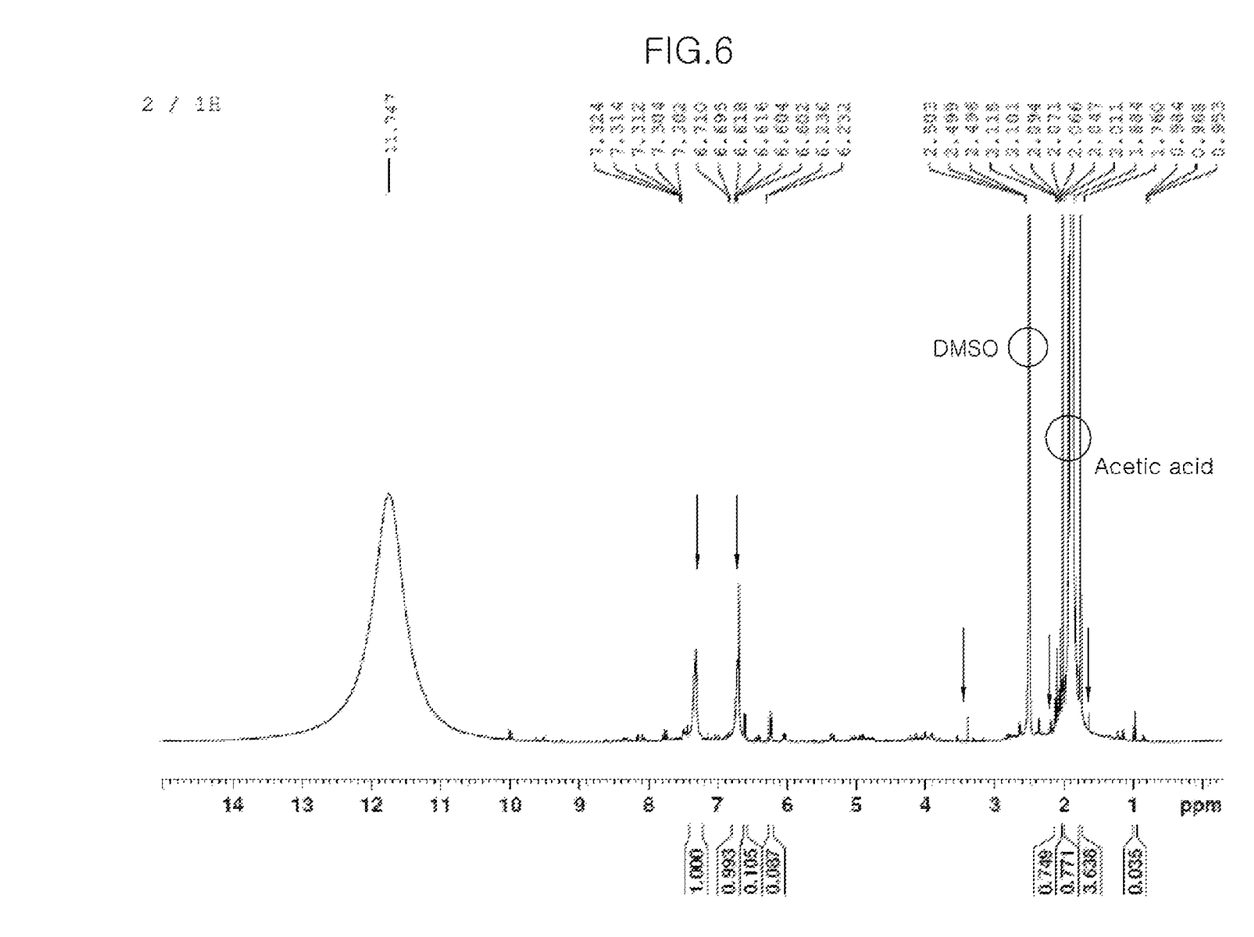
FIG. 6 shows the analysis of nuclear magnetic resonance (NMR) spectroscopy of an adipamide produced according to an embodiment of the present invention.

In Test Example 1, a sample prepared in one Example of the present invention was analyzed by nuclear magnetic resonance (NMR) spectroscopy in order to confirm the components of the sample. The NMR spectrum of the sample was analyzed by a Bruker AVIII400 instrument in $CDCl_3$ and dimethyl sulfoxide (DMSO) using trimethylsilane (TMS) as an internal standard ($^1H$ at 400 MHz, and $^{13}C$ at 100 MHz).

Nuclear magnetic resonance spectroscopy is an analytical method for identifying a compound, which makes it possible to determine an atom to which a hydrogen atom in the compound bonds, and to determine a functional group containing the atom, and to determine the spatial arrangement of the compound.

The results of the hydrogen nuclear magnetic resonance spectroscopy are shown in FIG. 6. Four peaks at 7.21 ppm, 6.67 ppm, 2.03 ppm and 1.47 ppm appeared in the hydrogen nuclear magnetic resonance spectroscopy, indicating that adipamide was synthesized.

The nuclear magnetic resonance spectroscopy data obtained in analysis of the sample prepared in the Example of the present invention suggest that the desired adipamide was produced.

Meanwhile, as shown in reaction scheme 4 below, adipamide produced according to the present invention can be converted into adipic acid by performing a hydrolysis reaction in an acidic aqueous solution at a temperature of about 100° C.

Reaction Scheme 4

Conventional processes of synthesizing a raw material for nylon 66 from a petrochemical compound generally have a problem in that a strongly toxic compound is used or the yield is very low. However, the production method according to the present invention makes it possible to produce the intermediate adipamide, which can be converted into adipic acid, in high yield at low costs through a significantly simple process from glucose derived from biomass such as environmentally friendly plant resources. Accordingly, adipic acid produced from the intermediate adipamide can be used as a raw material for nylon which is used for vehicle parts.

As described above, the method for producing adipamide according to the present invention has the advantage of producing the intermediate adipamide, which can be converted into adipic acid, in high yield at low costs by a significantly simple process compared to a conventional petrochemical method based on petrochemicals. Thus, adipic acid produced from the adipamide can be used as a raw material for producing nylon 66, which is used as an automobile part material, by use of bio-based adipic acid. Therefore, the method of the present invention is expected to have significant economic and industrial ripple effects.

While the present invention has been described with respect to the various exemplary embodiments, it will be apparent to those skilled in the art that various changes and modifications may be made without departing from the spirit and scope of the invention as defined in the following claims.

What is claimed is:

1. A method for producing adipamide, comprising the steps of:
   (a) producing a glucaric acid potassium salt by one or more steps comprising reacting glucose, nitric acid ($HNO_3$), sodium nitrite ($NaNO_2$) and potassium hydroxide (KOH);
   (b) producing glucamide by reacting the glucaric acid potassium salt and an acidic solution and removing a potassium ion from the glucaric acid potassium salt;
   (c) preparing a reaction admixture by adding the glucamide and a catalyst to hydrogen halide and acetic acid; and
   (d) treating the reaction admixture and hydrogen gas in a reactor thereby producing the adipamide,
   wherein in the step (b), the method comprises: removing a potassium ion from the glucaric acid potassium salt by reacting a second mixture comprising the glucaric acid potassium salt and a reaction solvent with the acidic solution; and
   adding an aqueous ammonia solution to a substance from which the potassium ion was removed and then adding ethanol thereto to precipitate glucamide particles, and recovering the precipitated glucamide particles.

2. The method of claim 1, wherein the halogen halide is hydrogen bromide (HBr).

3. The method of claim 2, wherein the hydrogen bromide is included in an amount of 1 vol % to 2 vol % relative to the acetic acid.

4. The method of claim 1, wherein the glucamide in step (c) is added in an amount of 1 wt % to 2 wt % based on the total weight of the halogen halide and the acetic acid.

5. The method of claim 1, wherein the catalyst in step (c) comprises a RePd/$CeO_2$ catalyst or a Pt/$SiO_2$ catalyst.

6. The method of claim 5, wherein the RePd/$CeO_2$ catalyst comprises an amount of about 2 wt % to 10 wt % of rhenium (Re) and an amount of about 1 wt % to 3 wt % of palladium (Pd) based on the total weight of cerium oxide ($CeO_2$).

7. The method of claim 5, wherein the Pt/$SiO_2$ catalyst comprises an amount of about 1 wt % to 5 wt % of platinum (Pt) based on the total weight of silica ($SiO_2$).

8. The method of claim 1, wherein the reaction admixture comprises the catalyst in step (c) in an amount of about 0.3 wt % to 0.5 wt % based on the total weight of the reaction admixture.

9. The method of claim 1, wherein the hydrogen gas in step (d) is introduced into the reactor such that an internal pressure of the reactor is about 30 bar to 50 bar.

10. The method of claim 1, wherein the reaction in step (d) is performed at a temperature of about 120° C. to 150° C. for about 2 to 10 hours.

11. The method of claim 1, wherein, in the step (a), the method comprises:

preparing a reactant by reacting sodium nitrite ($NaNO_2$) and a first mixture comprising glucose and nitric acid ($HNO_3$);

preparing a basic reactant having a pH of about 9 to 10 by adding potassium hydroxide (KOH) the reactant;

preparing an acidic reactant having a pH of about 3 to 4 by adding nitric acid (HNO3) to the basic reactant; and precipitating the acidic reactant, and filtering and washing the formed precipitate to recover a glucaric acid potassium salt.

12. The method of claim 11, wherein the sodium nitrite ($NaNO_2$) and the first mixture is reacted at a temperature of about 0 to 30° C.

13. The method of claim 1, wherein the glucose and the sodium nitrite in step (a) are reacted at a weight ratio of about 1:500 to 1:1500.

14. The method of claim 1, wherein the reaction solvent is any one or more selected from the group consisting of C1 to C10 primary alcohols and secondary alcohols.

15. The method of claim 1, wherein the acidic solution is sulfuric acid ($H_2SO_4$) or para-toluene sulfuric acid.

16. The method of claim 1, wherein the reacting the second mixture with the acidic solution is perfothied for about 12 to 24 hours.

17. The method of claim 1, wherein the aqueous ammonia solution has an ammonia concentration of about 25 wt % to 28 wt % based on the total weight of the aqueous ammonia solution.

18. A method of producing an adipic acid comprising, producing adipamide by a method of claim 1.

19. A nylon product comprising an adipic acid produced by a method of claim 18.

* * * * *